(12) United States Patent
Griswold

(10) Patent No.: US 6,310,174 B1
(45) Date of Patent: Oct. 30, 2001

(54) PRIMARY ALKANOLAMIDES

(75) Inventor: Karl E. Griswold, Austin, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/560,229

(22) Filed: Apr. 28, 2000

Related U.S. Application Data

(60) Provisional application No. 60/132,063, filed on Apr. 30, 1999.

(51) Int. Cl.[7] .................................................. C08G 69/34
(52) U.S. Cl. .................................... 528/339.3; 528/339.5; 525/420.5; 554/103
(58) Field of Search ....................... 525/420.5; 528/339.3, 528/339.5, 342; 554/103; 508/555

(56) References Cited

U.S. PATENT DOCUMENTS

| | | | |
|---|---|---|---|
| 4,239,635 | 12/1980 | Rieder | 252/34 |
| 4,293,432 | 10/1981 | Papay et al. | 252/49.9 |
| 4,344,861 | 8/1982 | Levy | 252/391 |
| 4,439,336 | 3/1984 | Zaweski | 252/32.7 |
| 4,557,846 | 12/1985 | Wisotsky | 252/51.5 |
| 4,822,507 | 4/1989 | Kanamori et al. | 252/49.5 |
| 4,912,196 | 3/1990 | Leoni et al. | 528/339.3 |
| 4,941,983 | 7/1990 | Coates et al. | 252/8.515 |
| 5,006,170 | 4/1991 | Schwarz et al. | 106/20 |
| 5,576,416 | * 11/1996 | Walker | 528/340 |
| 5,880,072 | 3/1999 | Furey et al. | 508/263 |
| 6,046,282 | 4/2000 | Starner et al. | 525/432 |
| 6,214,914 | * 4/2001 | Evans et al. | 524/323 |

FOREIGN PATENT DOCUMENTS

| | | |
|---|---|---|
| 26 47 979 | 4/1977 | (DE) . |
| 0 467 533A1 | 1/1992 | (EP) . |
| 09100490 | 4/1997 | (JP) . |

OTHER PUBLICATIONS

International Search Report—Date of Mailing Jul. 25, 2000.

* cited by examiner

Primary Examiner—James J. Seidleck
Assistant Examiner—Melanie Bagwell
(74) Attorney, Agent, or Firm—O'Keefe, Egan & Peterman LLP

(57) ABSTRACT

This invention concerns a composition containing a dimerized or trimerized fatty acid amide of a primary alkanolamine that remains clear of suspended solids during storage, making mixtures containing the additive particularly useful to the metalworking industry. The amide may be formed by the condensation of a primary alkanolamine and a dimerized or trimerized fatty acid. When added to an amide of a primary alkanolamine and fatty acid containing a single carboxylic acid group, these molecules are able to prevent crystallization of the amide mixture.

14 Claims, No Drawings

PRIMARY ALKANOLAMIDES

This application claims priority to U.S. provisional application Serial No. 60/132,063, filed Apr. 30, 1999.

BACKGROUND OF INVENTION

This invention relates to compositions for use as corrosion inhibitors, lubricants and emulsifiers, particularly primary alkanoletheramides made from dimerized or trimerized tall oil fatty acids and from an aminoalkoxyalcohol such as aminoethoxyethanol, and compositions containing fatty acid mono-amides and the primary alkanoletheramides of dimer or trimer acids.

Alkanolamides are used in the metalworking industry as corrosion inhibitors, lubricants and emulsifiers. The industry often uses C10 to C24 fatty acids for production of these amides, including use of tall oil fatty acids (TOFA) which consist mainly of mixtures of saturated, mono-unsaturated and di-unsaturated C18 fatty acids. In the past the industry has typically used amides from secondary alkanolamines due to the tendency for these amides to remain free of precipitated solids during storage. These "clear" liquids have the advantage of being easy to handle and dispense. There now exists a push in the industry to move away from use of secondary alkanolamines due to health concerns. Primary alkanolamines present adequate replacements in many applications. However, fatty amides of primary alkanolamines tend to precipitate out solids at ambient temperatures and in some cases become completely solid. This makes these mono-substituted alkanolamides difficult to handle.

SUMMARY OF INVENTION

This invention provides a solution to one or more of the problems and disadvantages discussed above. The current invention relates to a composition containing an amide of a primary amine that remains clear of suspended solids during storage, making mixtures containing the additive particularly useful to the metalworking industry. The composition contains an amide formed by the condensation of a primary amine and a dimerized or trimerized fatty acid. Preferably, the primary amine is an alkanoletheramine such as of formula $H(OA)_a NH_2$ wherein A is independently in each occurrence a diradical of ethyl or propyl and "a" is from 2 to about 30. The dimer and trimer acids are produced by linking two or three monounsaturated acid molecules at the site of unsaturation resulting in loss of unsaturation and various linkages joining the two or three molecules at some point on their fatty carbon chains. The condensation reaction of this acid with aminoethoxyethanol, for instance, produces a molecule with two or three substituted amide functionalities and two to three adjoining fatty acid chains. Advantageously, when added to an amide of a primary alkanolamine and monomeric fatty acid, these molecules are able to prevent crystallization of the amide mixture. Formation of a dimer amide may be represented by the following reaction scheme:

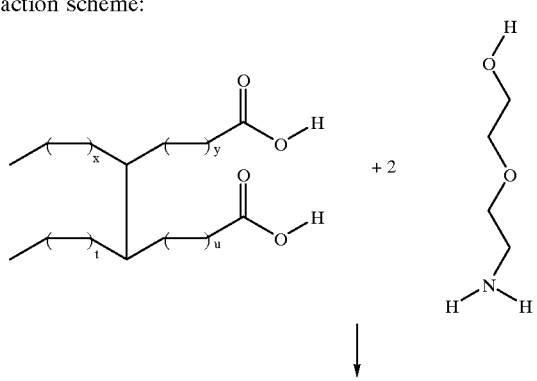

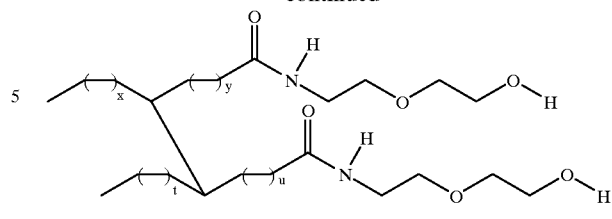

In this scheme, the total number of carbons in the fatty acid may vary widely (each of x, y, t and u may vary from 1 to 25) and in one embodiment is 36. This is but one possible structure arrived at by dimerization and is not intended to be limiting in any way. The product shown is derived from aminoethoxyethanol, but other amines may be employed.

Formation of a trimer amide may be represented by the following reaction scheme:

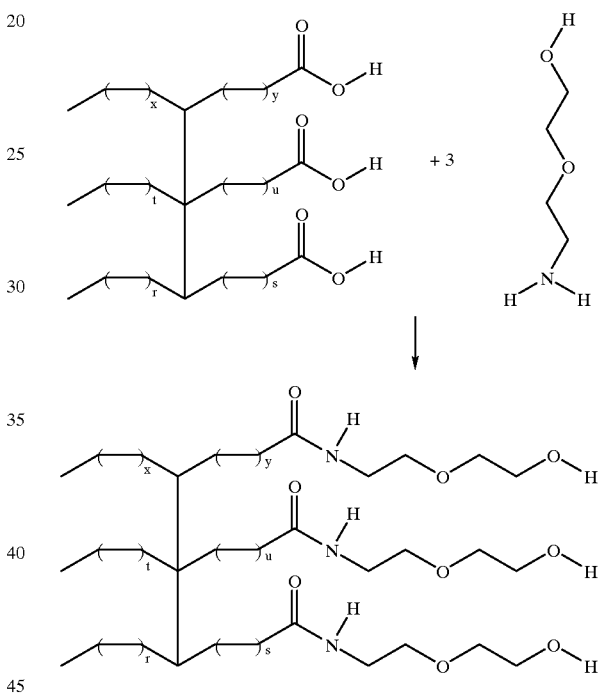

In this scheme, the total number of carbons in the fatty acid may vary widely (each of x, y, t, u, r and s may vary from 1 to 25) and in one embodiment is 54. This is but one possible structure arrived at by trimerization and is not intended to be limiting in any way. The product shown is derived from aminoethoxyethanol, but other amines may be employed.

In one broad respect, this invention is the reaction product of a mono-amine and a dimerized or trimerized fatty acid. In another broad respect, this invention is a manufacturing process, comprising: contacting an amine and a dimerized or trimerized fatty acid to form a reaction product. In one broad respect, this invention is a primary alkanoletheramide of a dimerized or trimerized fatty acid. In another broad respect, this invention is a composition comprising the reaction product of a primary aminoalkoxyalkanol and a dimerized or a trimerized fatty acid. A representative, non-limiting example of a suitable aminoalkoxyalkanol is aminoethoxyethanol. In another broad respect, this invention is a composition containing a mono-amide made from a primary alkanolamine and a poly-amide made from a dimer or trimer acid and from a primary amine.

In another broad respect, this invention is a composition comprising a compound of formula

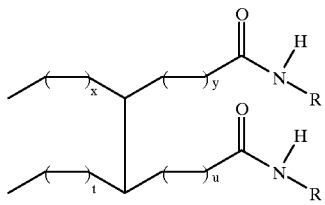

wherein each of x, y, t and u may vary from 1 to 25 and wherein R is an alkanol or an ether-alkanol radical.

In another broad respect, this invention is a composition comprising a compound of formula

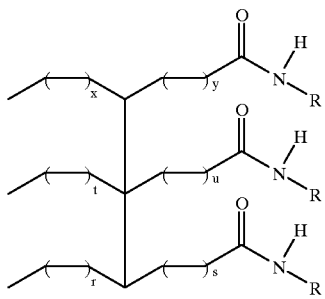

wherein each of x, y, t, u, r and s may vary from 1 to 25 and wherein R is an alkanol or an ether alkanol radical.

DETAILED DESCRIPTION OF THE INVENTION

Fatty acids (TOFA) used in making the amides of this invention are dimerized or trimerized using known procedures. The fatty acids to be dimerized or trimerized are typically monosaturated and may contain about 8–20 carbon atoms. The fatty acid may be an unsaturated fatty acid such as hypogeic acid, oleic acid, linoleic, elaidic acid, erucic acid, brassidic acid, tall oil fatty acids and the like. In addition, diacids based on these acids may be used.

Among the diacids which may be used are alkylene dicarboxylic acids containing from 2 to about 12 carbon atoms. It is also contemplated within the scope of this invention that aromatic dicarboxylic acids, such as phthalic acid, also may be used. Examples of alkylene dicarboxylic acids include oxalic acid, malonic acid, succinic acid, glutaric acid, adipic acid, pimelic acid, suberic acid, azaleic acid, sebacic acid, etc. Such dicarboxylic acids may also be substituted by an alkyl, an alkenyl, a cycloalkyl, an hydroxyl, or alkoxyl group as was heretofore described. The unsaturated fatty acids may also be substituted by an alkyl, an alkenyl, a cycloalkyl, an hydroxyl, or alkoxyl group as was heretofore described. Representative general structures of such dimers and trimers are shown above. In general, the dimers and trimers are made by dimerization of unsaturated fatty acids, such as described in "The Dimer Acids," Edited by Edward C. Leonard (1975). Dimer and trimer acids are available commercially from Henkel Corporation, sold presently as EMPOL™ Dimer and Polybasic Acids.

The amines which can be used in this invention generally are primary amines and may be monoamines, diamines, and other polyamines. The reaction products of this invention are the bis-amides or higher (such as tri-amide) resulting from the reaction of each carboxyl group of the fatty acid with a primary amino group. Monoamines which may be utilized are alkyl amines containing from 2 to about 40 carbon atoms, but preferably from about 5 to about 25 carbon atoms. Examples of suitable alkyl groups include ethyl, propyl, butyl, pentyl, hexyl, hectyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, and pentacosyl. Normally the alkyl group is linear; however, branched alkyl groups also may be used but not necessarily with equivalent results. The alkyl group may be either saturated or unsaturated, i.e., the carbonaceous portion may contain one or more olefinic bonds. The aforementioned alkyl groups commonly have their commercial origin in fatty acids, and consequently often are supplied as mixtures. Therefore it is to be understood that amines containing a combination of the aforementioned groups are explicitly within the scope of this invention. It also is contemplated that alkyl groups which are substituted with an hydroxy or alkoxy group or both a hydroxy and alkoxy group are also within the scope of this invention. Alkoxyalkylamines, where the alkoxy portion contains from about 5 to about 18 carbon atoms, may be effectively employed as amines of this invention. Also, aminoalkoxyalkanols of from 4 to 18 carbons may be used, such as aminoethoxyethanol. The aminoalkoxyalkanol may contain multiple alkoxy components (a polyether). In this regard, the amines that may be employed in the practice of this invention include polyetheramines. The polyetheramines used in this invention are monoamines having up to about 200 carbon atoms, such chemicals including but not limited to hydroxyl, amine, and aminoalcohol functionalized polyether materials. Preferred polyetheramines have a molecular weight of from about 1,000 to about 3,000. Suitable monoamines include JEFFAMINE™ M-1000, JEFFAMINE™ M-2070, and JEFFAMINE™ M-2005.

Cycloalkylamines also may be suitable in this invention where the cycloalkyl ring contains from about 5 to about 10 carbon atoms and cycloalkyl groups containing 5, 6, or 8 carbon atoms are preferred. Examples of such groups include cyclopentyl, cyclohexyl, cycloheptyl, cyclooctyl, cyclononyl, and cyclodecyl. The ring portion of such groups may also contain other alkyl, alkenyl, hydroxyl, and alkoxyl moieties, or any combination of these moieties.

Heterocyclic amines often afford products which are effective corrosion inhibitors; however, it is noteworthy that these heterocyclic amines are not primary amines. Examples of suitable heterocyclic amines, enumerated solely for purposes of illustration and not by way of limitation, are phenothiazine and morpholine.

Another class of amines used in this invention are diamines containing one primary amino group. The diamines of this invention are alkylenediamines, wherein the alkylene group consists from 2 to about 10 carbon atoms. Examples of suitable diamines include ethylenediamine, propylenediamine, butylenediamine, pentylenediamine, hexylenediamine, etc. Especially desirable are propylenediamines. The diamines of this invention are substituted at one nitrogen atom with an alkyl, alkenyl, or cycloalkyl group, or substituted alkyl, alkenyl, or cycloalkyl group wherein these groups conform to the description given above.

Terminally N-substituted polyamines also are contemplated as being within the scope of this invention. Such polyamines include diethylenetriamine, triethylenetetramine, tetraelhylenepentamine, pentaethylenehexamine, etc. The terminal substituents may be an alkyl, alkenyl, or cycloalkyl group, or substituted alkyl, alkenyl, or cycloalkyl group wherein these groups conform to the description previously given.

Preferred in the practice of this invention are alkanoletheramines which contain a single primary amine group. The alkanoletheramines may be represented by the formula:

H(OA)$_a$NH$_2$ wherein A is independently in each occurrence a diradical of propane or ethane (i.e., —CH$_2$CH$_2$—, or —CHCH$_3$CH$_2$— or —CH$_2$CHCH$_3$—), and "a" may be from 2 to 30. It is envisioned that other functional groups may be attached to the alkanoletheramines. A representative example of a useful alkanoletheramine is HO—CH$_2$CH$_2$—O—CH$_2$CH$_2$—NH$_2$ (2,2'-aminoethoxyethanol)

The reaction products of this invention may be prepared by reacting one molar proportion of amine with one equivalent of a carboxylic acid under reaction conditions for a time sufficient to produce one molar proportion of water. Thus, if a trimerized fatty acid is employed as the starting material, at least about three moles of mono-primary amine will be used. A solvent is employed advantageously and should be high boiling (100°–200° C.), inert, and should form an azeotrope with water. Aromatic solvents are especially convenient, and examples of these include toluene, xylene, tri-methylbenzenes, and so forth. The volume of solvent used approximates the sum of the weight of amine and acid employed. The mixture is then heated so as to distill the azeotrope of the solvent and water, most advantageously returning the solvent to the reaction mixture. The condensate is collected and heating is continued until the theoretical amount of water has been collected. It is to be noted that the proportion of reactants used is about one mole of amine per one equivalent (one-half mole) of acid. Therefore, one mole of water will be collected per mole amine employed. To accelerate formation of the reaction product, a small amount of a strong acid may be used as a catalyst. For example, p-toluenesulfonic acid at a concentration from about 1 to about 10 mole percent may be employed advantageously.

Mixtures of symmetrical and unsymmetrical amides may be formed, at least in part, when a mixture of 2 amines is used. Such unsymmetrical amides may have particularly desirable anti-corrosion properties. Therefore, it is to be understood explicitly that the reaction product from a combination of amines in a total ratio of one mole with one equivalent of dicarboxylic acid is within the scope of this invention.

The amount of the amides of dimer or trimer fatty acids of this invention necessary to inhibit corrosion will depend on the nature of the amide, the type of usage contemplated, and the identity and quantity of corrosive agents present in the petroleum or petroleum product contacting metal surfaces. Surprisingly, the amides of the dimer or trimer fatty acids have been found to stabilize mono-amides from crystallization. When the dimer or trimer amides of this invention are employed in combination with a mono-amide made from a primary amine to form a stabilized composition, the amount of dimer or trimer amide may be any amount effective to increase the time when crystallization of the composition occurs. In general, this amount may vary from about 0.1 to about 10 percent by weight based on the total weight of the two compounds. In on embodiment, the amount is from about 1 to about 10.

The mono-amides used in this invention are well known materials. Many types are available commercially. In general, the mono-amides are made by reacting any of the amines described above with a fatty acid that contains a single carboxylic acid group. The reaction of the amines with the fatty acid can be conducted using well known techniques.

The following examples are illustrative of this invention and are not intended to be limit the scope of the invention or claims hereto. Unless otherwise denoted all percentages are by weight. In the tables, "N/A" denotes "not available" and "TOFA" denotes tall oil fatty acid.

EXAMPLE 1

Production of 2:1 2,2'-aminoethoxyethanol:TOFA 2,2'-Aminoethoxyethanol (DGA® Agent) and TOFA (5% rosin) were reacted in a 2 to 1 amine to acid molar ratio. The combined reactants were heated to 157 degrees Centigrade and held at this temperature for five hours. Water removal from the reaction during this period was facilitated by a slow flow of nitrogen. The product was isolated as a brown liquid. Upon storing at ambient temperature for 3–4 days the product began to precipitate out white solids. The equilibrated product was found to be a slurry of white solids in brown liquid.

EXAMPLE 2

Production of 1:1 2,2'-Aminoethoxyethanol-Dimer Amide 2,2'-Aminoethoxyethanol and dimerized fatty acid were reacted in a 2.12 to 1 amine to acid molar ratio. The combined reactants were heated to 155 degrees Centigrade and held at this temperature for 2.5 hours. Water removal from the reaction during this period was facilitated by a slow flow of nitrogen. The product was isolated as a viscous brown liquid.

EXAMPLE 3

Production of 1:1 2,2'-Aminoethoxyethanol-Trimer Amide 2,2'-Aminoethoxyethanol and trimerized fatty acid were reacted in a 3.18 to 1 amine to acid molar ratio. The combined reactants were heated to 155 degrees Centigrade and held at this temperature for 2.5 hours. Water removal from the reaction during this period was facilitated by a slow flow of nitrogen. The product was isolated as a viscous brown liquid.

EXAMPLE 4

This example demonstrates the ability of the compositions of this invention to remain clear during storage at ambient temperatures. Seven commercial pour point depressants were used as additives in samples of the 2:1 amide of example 1. The pour point depressants and weight percentages in the resulting compositions are shown in Table 1. At a 1% treatment level, the amides were found to develop solids at approximately 12 days for both additives. At the higher treatment levels of 2% by weight, both additives were seen to separate from the amides after 14 days demonstrating their incompatibility at higher concentrations.

TABLE 1

| Blend | Amide | Pour point depressant (Lubrizol 6662) | Pour point depressant (Lubrizol 662A) | Days to Crystallization |
|---|---|---|---|---|
| A | 100 | 0 | 0 | 3 |
| B | 99 | 1 | 0 | 10–12 |
| C | 98 | 2 | 0 | Incompatible after 14 |
| D | 99 | 0 | 1 | 10–12 |
| E | 98 | 0 | 2 | Incompatible after 14 |

EXAMPLE 5

Evaluation of Trimer Amides as Rheology Modifiers

Samples of the amide of example 1 were mixed with TOFA acid only, neodecanoic acid only, aminoethoxyethanol-trimer amide only and several combinations of TOFA and neodecanoic acid with aminoethoxyethanol-trimer amide. These samples were evaluated for clarity on a daily basis wherein temperature was maintained at about 21–24 degrees Centigrade. All samples remained free of solids in excess of 30 days. Neat 2:1 amide was known to develop solids at ambient temperature after 3–4 days. Results are shown in Table 2 for a period of 155 days. In Table 2, amide 1 refers to the amide made in example 1, amide 2 refers to the dimer amide made in example 2 and amide 3 refers to the trimer made in example 3.

TABLE 2

Clarity of aminoethoxyethanol-TOFA amides at Ambient Temperature

| COMPOSITION | DAYS CLEAR |
|---|---|
| Amide 1 | 3 |
| Amide 1/Amide 3 at 3% | 41 |
| Amide 1/Amide 3 at 5%[1] | 115 |
| Amide 1/Amide 3 at 10% | 155 |
| Amide 1/TOFA Salt | 108 |
| Amide 1/TOFA Salt/3% Amide 3 | 155 |
| Amide 1/TOFA Salt/5% Amide 3 | 155 |
| Amide 1/TTOFA Salt/10% Amide 3 | 155 |
| Amide 1/neodecanoic acid salt | 35 |
| Amide 1/neodecanoic acid salt/3% Amide 1 | 155 |
| Amide 1/neodecanoic acid Salt/5% Amide 3 | 155 |
| Amide 1/neodecanoic acid Salt/10% Amide 3 | 155 |

[1]Solids formed when ambient temperature dropped below 15 degrees Centigrade overnight. Solids did not dissolve when room temperature again reached 21–24 degrees Centigrade.

The amides were also evaluated for clarity at 15 degrees Centigrade. The results after 44 days are shown in Table 3.

TABLE 3

Clarity of Amides at Subambient Temperature

| Amide 1 | 0.1 |
|---|---|
| Amide 1/3% Amide 3 | 1 |
| Amide 1/5% Amide 3 | 1 |
| Amide 1/10% Amide 3 | 2 |
| Amide 1/TOFA salt | 1 |
| Amide 1/TOFA salt/3% Amide 3 | 37 |
| Amide 1/TOFA salt/5% Amide 3 | 44 |
| Amide 1/TOFA salt/10% Amide 3 | 44 |
| Amide 1/neodecanoic acid salt | 0.2 |
| Amide 1/neodecanoic acid salt/3% Amide 3 | 4.5 |
| Amide 1/neodecanoic acid salt/5% Amide 3 | 8 |
| Amide 1/neodecanoic acid salt/10% Amide 3 | 44 |

In reviewing the data in Tables 2 and 3, it may be seen that addition of the Amide 3 (the trimer amide) to any DGA-TOFA amide or amide/salt mixture greatly improves the clarity of the sample. It is also seen that the higher the content of timer amide in any particular blend, the greater the clarity of the sample, especially at subambient temperatures.

EXAMPLE 5

This example was conducted using monoisopropanolamine (MIPA) to form the amides from TOFA and using the procedure of the examples above. In this example, "MEA" denotes monoethanolamine. The results are shown in Tables 4 and 5 for tests of 63 days.

TABLE 4

Clarity of MIPA-TOFA Amides at Ambient Temperature

| Amide Blend | Days to Crystallization |
|---|---|
| MIPA-TOFA | 3 |
| MIPA-TOFA/Amide 3 at 3% | 63 |
| MIPA-TOFA /Amide 3 at 5% | 63 |
| MIPA-TOFA /Amide 3 at 10% | 63 |
| MIPA-TOFA/MIPA, TOFA Salt/3% Amide 3 | 63 |
| MIPA-TOFA /TOFA Salt/3% Amide 3 | 63 |
| MIPA-TOFA /TOFA Salt/5% Amide 3 | 63 |
| MIPA-TOFA /TOFA Salt/10% Amide 3 | 63 |

TABLE 5

Clarity of MIPA-TOFA Amides at Subambient Temperature (15° C.)

| Amide Blend | Days to Crystallization |
|---|---|
| MIPA-TOFA | 0.3 |
| MIPA-TOFA/Amide 3 at 3% | 1 |
| MIPA-TOFA /Amide 3 at 5% | 1.5 |
| MIPA-TOFA /Amide 3 at 10% | 1.5 |
| MIPA-TOFA/MIPA, TOFA Salt/3% Amide 3 | 63 |
| MIPA-TOFA /TOF4 Salt/3% Amide 3 | 63 |
| MIPA-TOFA /TOFA Salt/5% Amide 3 | 63 |
| MIPA-TOFA /TOFA Salt/10% Amide 3 | 63 |

Examination of this data shows that addition of the trimer amide (Amide 3), especially in the presence of an acid/amine salt, greatly improves the clarity of the subject amide. Again, the higher the concentration of the trimer amide, the greater the clarity of the blend. These experiments also demonstrate the wide range of utility of the trimer amide in that it is effective with different semicrystalline amides and in conjunction with various alkanol/acid salts.

EXAMPLE 7

An experiment was carried out on a commercially available DGA-TOFA amide that was known to precipitate solids at ambient temperatures. The trimer amide was added to this material at 1, 3 and 5 percent by weight. These samples were stored at ambient temperature and examined for solid formation on a daily basis. The results are shown in Table 6 for a 97 day run. In this experiment, a mixture with 1% trimer crystallized after ambient temperature dropped below 15 degrees Centigrade overnight.

TABLE 6

Comparative Study of Clarity for DGA-TOFA Amides at Ambient Temperature (about 22° C.)

| Amide Blend | Days to Crystallization |
|---|---|
| Commercial DGA-TOFA Amide | 32 |
| Commercial DGA-TOFA Amide /1% Amide 3 | 50 |
| Commercial DGA-TOFA Amide /3% Amide 3 | 97 |
| Commercial DGA-TOFA Amide /5% Amide 3 | 97 |

This data also shows the effectiveness of the timer amide in preventing crystal formation in amide blends. This experiment also demonstrates the usefulness of the trimer amide with alkanolamides derived from varying grades of TOFA acid. Previous experiments were performed with amides from 5% rosin TOFA. Finally, this example shows that the trimer amide is able to effectively modify the physical state of some commercial products (at about 22 degrees Centigrade) as a lone additive without further modification of the existing commercial amide.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as illustrative embodiments. Equivalent elements or materials may be substituted for those illustrated and described herein, and certain features of the invention may be utilized independently of the use of other features, all as would be apparent to one skilled in the art after having the benefit of this description of the invention.

What is claimed is:

1. A method useful for stabilizing a mono-amide of a fatty acid from crystallizing, comprising: adding to the mono-amide a reaction product of an aminoalkoxyalcohol and a dimerized or trimerized fatty acid.

2. The method of claim 1 wherein the aminoalkoxyalcohol is of formula $H(OA)_a NH_2$ wherein "a" is from 2 to 30, and A is independently in each occurrence a diradical of ethane or propane.

3. The method of claim 1 wherein the aminoalkoxyalcohol is aminoethoxyethanol.

4. A composition, comprising:
   a mono-amide of a fatty acid, and
   a reaction product of an aminoalkoxyalcohol and a dimerized or trimerized fatty acid.

5. The composition of claim 4, wherein the aminoalkoxyalcohol is of formula $H(OA)_a NH_2$ wherein A is independently in each occurrence a diradical of ethane or propane, and "a" is from 2 to 30.

6. The composition of claim 1 wherein the dimerized or trimerized fatty acid is made from a monosaturated fatty acid having from about 8 to about 20 carbons.

7. The method of claim 4 wherein the aminoalkoxyalcohol is aminoethoxyethanol.

8. A method useful for stabilizing a mono-amide of a fatty acid from crystallizing, comprising: adding to the mono-amide a reaction product of an amine and a dimerized or trimerized fatty acid, wherein the amount of reaction product is in the range from about 0.1 to 10 percent by weight based on the total weight of the mono-amide and the reaction product.

9. The method of claim 8 wherein the amine is an aminoalkoxyalcohol.

10. The method of claim 8 wherein the amine is of formula $H(OA)_a NH_2$ wherein "a" is from 2 to 30, and A is independently in each occurrence a diradical of ethane or propane.

11. A composition, comprising:
   a mono-amide of a fatty acid, and
   a reaction product of a primary amine and a dimerized or trimerized fatty acid wherein the amount of reaction product is in the range from about 0.1 to 10 percent by weight based on the total weight of the mono-amide and the reaction product.

12. The composition of claim 11, wherein the primary amine is of formula $H(OA)_a NH_2$ wherein A is independently in each occurrence a diradical of ethane or propane, and "a" is from 2 to 30.

13. The composition of claim 11 wherein the dimerized or trimerized fatty acid is made from a monosaturated fatty acid having from about 8 to about 20 carbons.

14. The composition of claim 11 wherein the primary amine is aminoethoxyethanol.

* * * * *